(12) United States Patent
Nelson et al.

(10) Patent No.: US 11,664,096 B2
(45) Date of Patent: May 30, 2023

(54) METHOD, APPARATUS AND COMPUTER PROGRAM PRODUCT FOR PERSONAL IDENTIFICATION AND ELECTRONIC DATA MANAGEMENT

(71) Applicants: University of Florida Research Foundation Incorporated, Gainesville, FL (US); The Board of Trustees of the Leland Stanford Junior University, Stanford, CA (US)

(72) Inventors: Eric Jorge Nelson, Gainesville, FL (US); Teja Vardhan Korrapati, Hyderabad (IN); Shivani Teegala, Hyderabad (IN); Hament Choudhary, Hyderabad (IN); Swastik Roy, Salt Lake City, UT (US); Stacey D. Maples, Palo Alto, CA (US); Dane Pieri, Brisbane, CA (US); Prasanna Sambandam Raghu, Hyderabad (IN)

(73) Assignees: UNIVERSITY OF FLORIDA RESEARCH FOUNDATION, INCORPORATED, Gainesville, FL (US); THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 745 days.

(21) Appl. No.: 16/610,304

(22) PCT Filed: May 2, 2018

(86) PCT No.: PCT/US2018/030730
§ 371 (c)(1),
(2) Date: Nov. 1, 2019

(87) PCT Pub. No.: WO2018/204537
PCT Pub. Date: Nov. 8, 2018

(65) Prior Publication Data
US 2020/0082921 A1 Mar. 12, 2020

Related U.S. Application Data

(60) Provisional application No. 62/500,169, filed on May 2, 2017.

(51) Int. Cl.
*G16H 10/60* (2018.01)
*H04L 43/0852* (2022.01)
(Continued)

(52) U.S. Cl.
CPC ............. *G16H 10/60* (2018.01); *G06V 40/13* (2022.01); *G06V 40/1347* (2022.01); *H04L 43/0852* (2013.01)

(58) Field of Classification Search
CPC ..... G06Q 10/10; G06F 16/9535; G16H 80/00
See application file for complete search history.

(56) References Cited

U.S. PATENT DOCUMENTS 9,818,154 B1 * 11/2017 Wilbert .............. H04N 1/00336
2002/0029157 A1 3/2002 Marchosky
(Continued)

OTHER PUBLICATIONS

International Searching Authority, International Search Report and Written Opinion for International Application No. PCT/US2018/030730, dated Aug. 29, 2018 (17 pages), USA.

*Primary Examiner* — Mahran Y Abu Roumi
(74) *Attorney, Agent, or Firm* — Alston & Bird LLP

(57) ABSTRACT

A method, apparatus, and computer program product are provided for identifying individuals using electronic fingerprint data, providing residence mapping functionality, resolving conflicts relating to the update of electronic records, and optimizing performance relating to the access of electronic records.

15 Claims, 16 Drawing Sheets

(51) Int. Cl.
*G06V 40/13* (2022.01)
*G06V 40/12* (2022.01)

(56) References Cited

U.S. PATENT DOCUMENTS

| | | | |
|---|---|---|---|
| 2003/0065957 A1* | 4/2003 | Tsuji | H04N 21/4181 |
| | | | 726/21 |
| 2008/0306872 A1 | 12/2008 | Felsher | |
| 2009/0024417 A1 | 1/2009 | Marks et al. | |
| 2009/0070148 A1* | 3/2009 | Skocic | G06F 16/24 |
| | | | 705/3 |
| 2010/0299158 A1 | 11/2010 | Siegel | |
| 2011/0307518 A1 | 12/2011 | Lewis et al. | |
| 2012/0150564 A1 | 6/2012 | Lese | |
| 2012/0171990 A1* | 7/2012 | Williams | H04W 4/24 |
| | | | 455/406 |

* cited by examiner

METHOD, APPARATUS AND COMPUTER PROGRAM PRODUCT FOR PERSONAL IDENTIFICATION AND ELECTRONIC DATA MANAGEMENT

GOVERNMENT LICENSE RIGHTS

This invention was made with government support under OD019893 awarded by National Institutes of Health. The government has certain rights in the invention.

TECHNOLOGICAL FIELD

An example embodiment of the present invention relates generally to personal identification and electronic data management, and more particularly, to a method, apparatus and computer program product for identifying individuals using electronic fingerprint data, providing residence mapping functionality, resolving conflicts relating to the update of electronic records, and optimizing performance relating to the access of electronic records.

BACKGROUND

The evolution of ubiquitous computing and desire for mobile access to electronic information has introduced a number of challenges in electronic data management. The particular environment from which the electronic data is requested may present connectivity and performance challenges.

The medical field in particular has a need for mobile support systems to access electronic information, decision support systems, and electronic health records. In some cases, mobile support systems may be deployed in remote areas, some of which are subject to limited network connectivity. The deployment of the clinical systems in remote areas having limited connectivity presents problems in accessing and accurately updating electronic records.

Additionally, social differences amongst various populations present challenges in accurately identifying a patient and correctly associating an electronic health record with the patient. Further, many patients reside in remote villages that may be easily identifiable using the mappings known to the clinical system or underlying geographic information system (GIS), presenting additional challenges in understanding geographical patterns in disease outbreak and other medical data.

BRIEF SUMMARY

A method, apparatus, and computer program product are therefore provided for identifying individuals using electronic fingerprint data, providing residence mapping functionality, resolving conflicts relating to the update of electronic records, and optimizing performance relating to the access of electronic records.

In some medical settings, numerous patients may visit a clinic seeking medical attention. To accurately maintain a set of patient records, the system needs to reliably identify the patients associated with the records. However, deploying traditional records management systems in various mobile clinics, each having a unique social setting, would require a uniform patient identification system where one may not exist.

Biometric information, such as electronic fingerprint data, can be used to improve accuracy of electronic health records management across variable environments. However, the fingerprints of young children may not be discernable, may be difficult to obtain, or may change over time as children mature such that new fingerprint scans of an individual may not be properly matched with prior scans of the individual that were taken when the individual was a child. Example embodiments described herein provide an innovative solution to these challenges of patient record matching using fingerprint data. In example embodiments, the fingerprints of individuals associated with a child (such as a relative) may be leveraged to associate the child with an existing or newly created electronic health record.

Example embodiments further provide for collection of patient residence information in culturally relevant ways and are designed to additionally log the treatment location in the electronic health record. Collection of this residency as a culturally relevant location hierarchy and treatment location dyad thus facilitate more granular data regarding disease outbreak pathways and other medical data.

Further, in remote clinical settings, practitioners may use mobile devices that experience limited connectivity. Some example embodiments described herein may therefore be designed to account for use on the mobile device even in an offline mode. For instance, during a patient encounter, several different practitioners may access and/or update a patient's electronic health record while operating offline, creating conflict issues when the user devices having conflicting electronic health records later connect to the network. Example embodiments described herein provide a conflict resolution process ensuring that the correct data is uploaded from the various user devices to a remote server and storage.

Example embodiments also optimize performance by intelligently syncing with the server according to signal availability and strength. Synchronization may be delayed during times of weak or no connectivity. In some examples where a mobile device is connected with a slow connection speed, data upload during synchronization may be performed in batches. Through the use of a dynamic synchronization design, example embodiments can minimize repetitively failed connectivity attempts, thereby improving performance and preserving battery life on the mobile device.

While example embodiments provided herein are described with respect to medical environments, health information systems and electronic health records, it will be appreciated that these descriptions are provided merely as an example, and embodiments are not limited to the medical field. Rather, the concepts described herein may be applied to the management of electronic data in any field.

A method for linking a patient to an electronic health record is provided. The method includes receiving an indication of an age of the patient and storing a subject fingerprint identifier in association with the electronic health record of the patient in an instance the age is greater than or equal to a lower age threshold. The method further includes storing an associated fingerprint identifier in association with the electronic health record of the patient in an instance the age is less than a higher age threshold.

A method is also provided for identifying an electronic health record associated with a patient. The method includes receiving an indication of an age of the patient, and, in an instance in which the age is less than a predefined age threshold, comparing a related fingerprint identifier associated with the patient to related fingerprint identifiers associated with electronic health records to attempt to identify the patient's electronic health record. In an instance in which the age is greater than or equal to the predefined age threshold, the method includes comparing a subject fingerprint identifier to fingerprint identifiers associated with electronic health records to attempt to identify the patient's electronic health record.

A method is also provided for receiving residence information comprising a culturally relevant location hierarchy, associating the residence information with an electronic health record, providing a geospatial distribution user interface comprising data extracted from a plurality of electronic health records in a geospatial distribution user interface, and enabling drill down interaction with the geospatial distribution user interface to change a level of detail of the extracted data.

A method is also provided for receiving an electronic record from a server to a first device, receiving an indication of a change to the electronic record via the first device, and attempting, by the first device, to synchronize the change to the electronic record on the server. The method further includes determining that another change has been made to the electronic record, and causing a prompt to be provided via a user interface of a second device to enable a user to resolve a conflict.

A method is provided that includes monitoring for a network connection, and, in an instance in which a network connection speed is identified and is below a predefined threshold but above or equal to a minimum threshold, transmitting synchronization data to a server via the network in batches. The method includes, in an instance in which the network connection speed is below the minimum threshold or no connection is available, caching the synchronization data and monitoring for an improved connection on a predefined time interval.

BRIEF DESCRIPTION OF THE DRAWINGS

Figure 1:
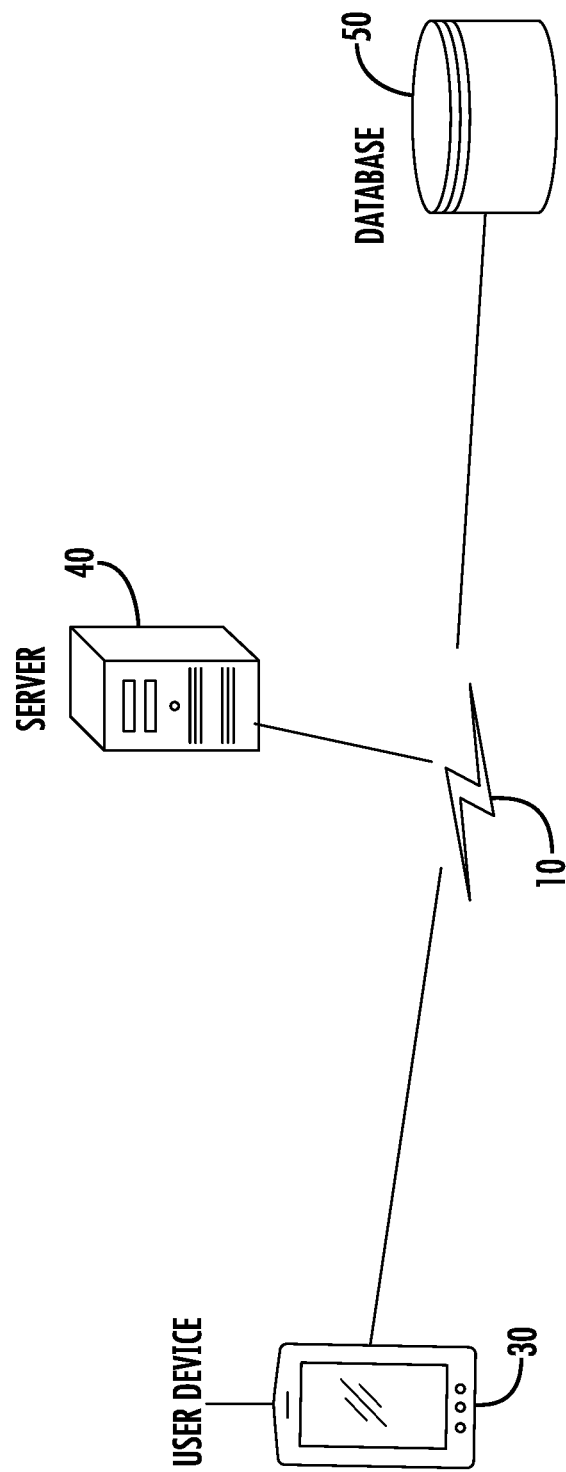
Figure 2:
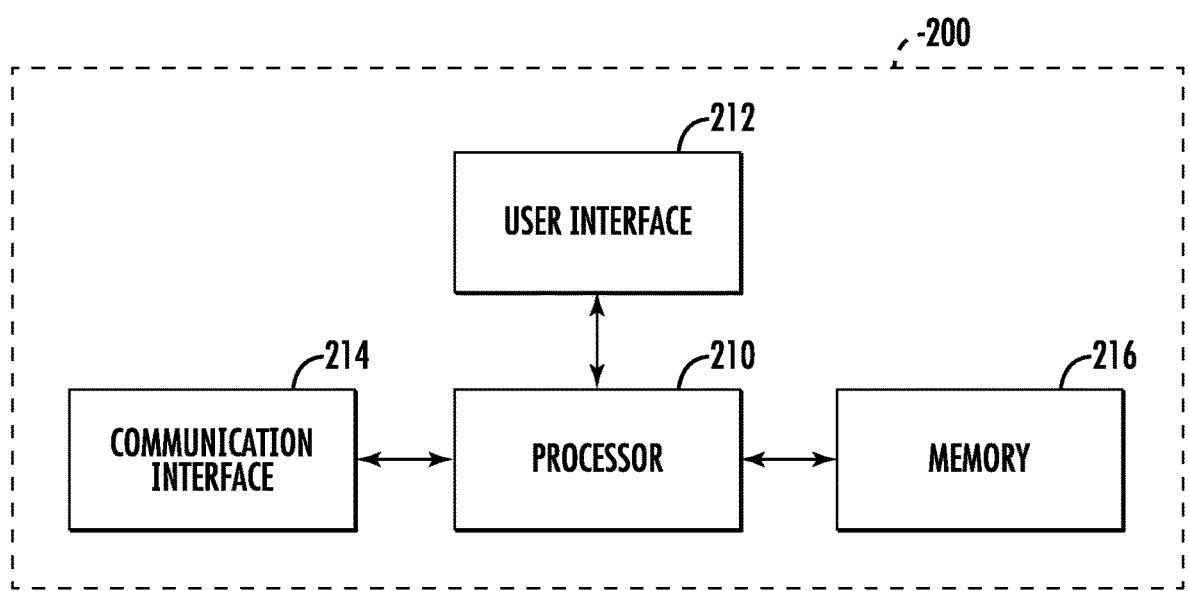
Figure 3:
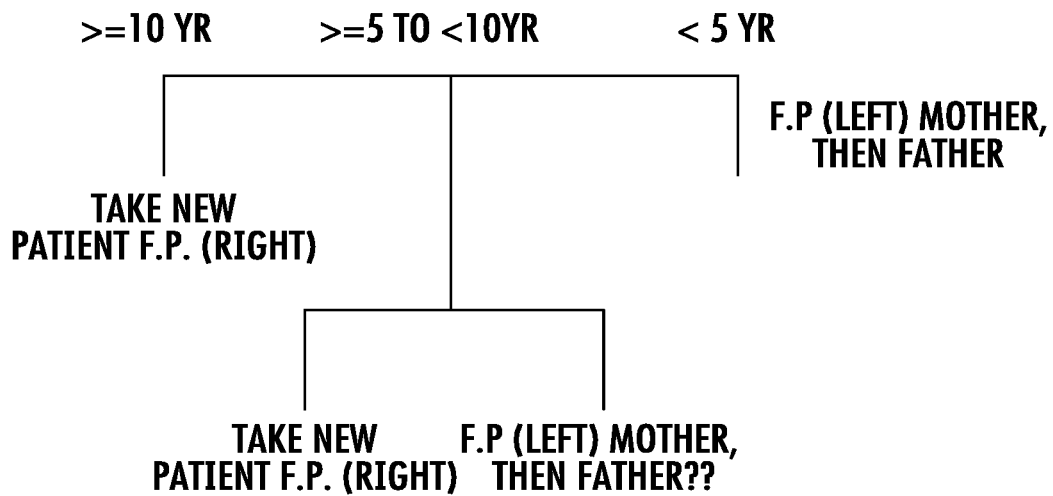
Figure 5A:
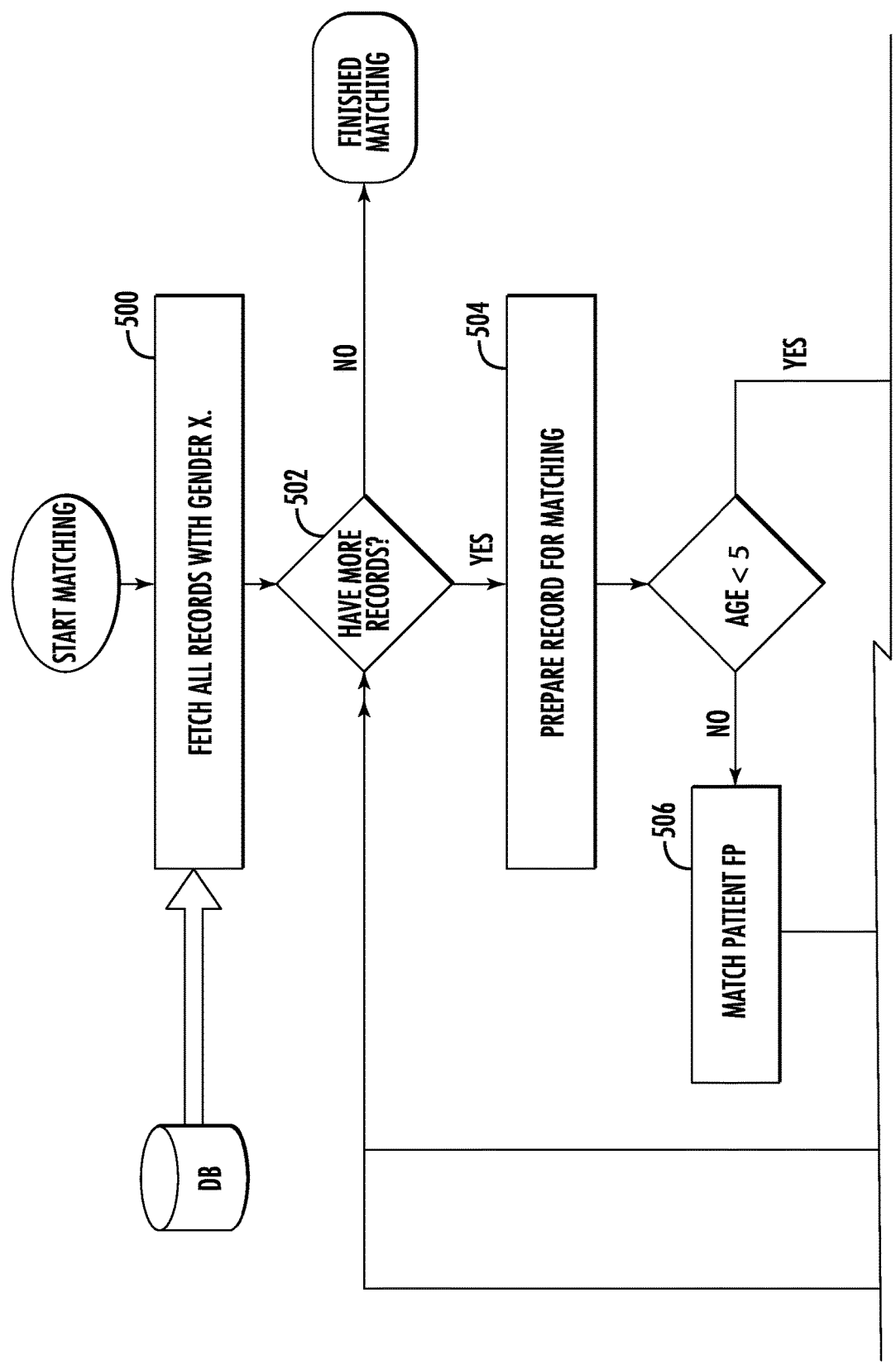
Figure 5B:
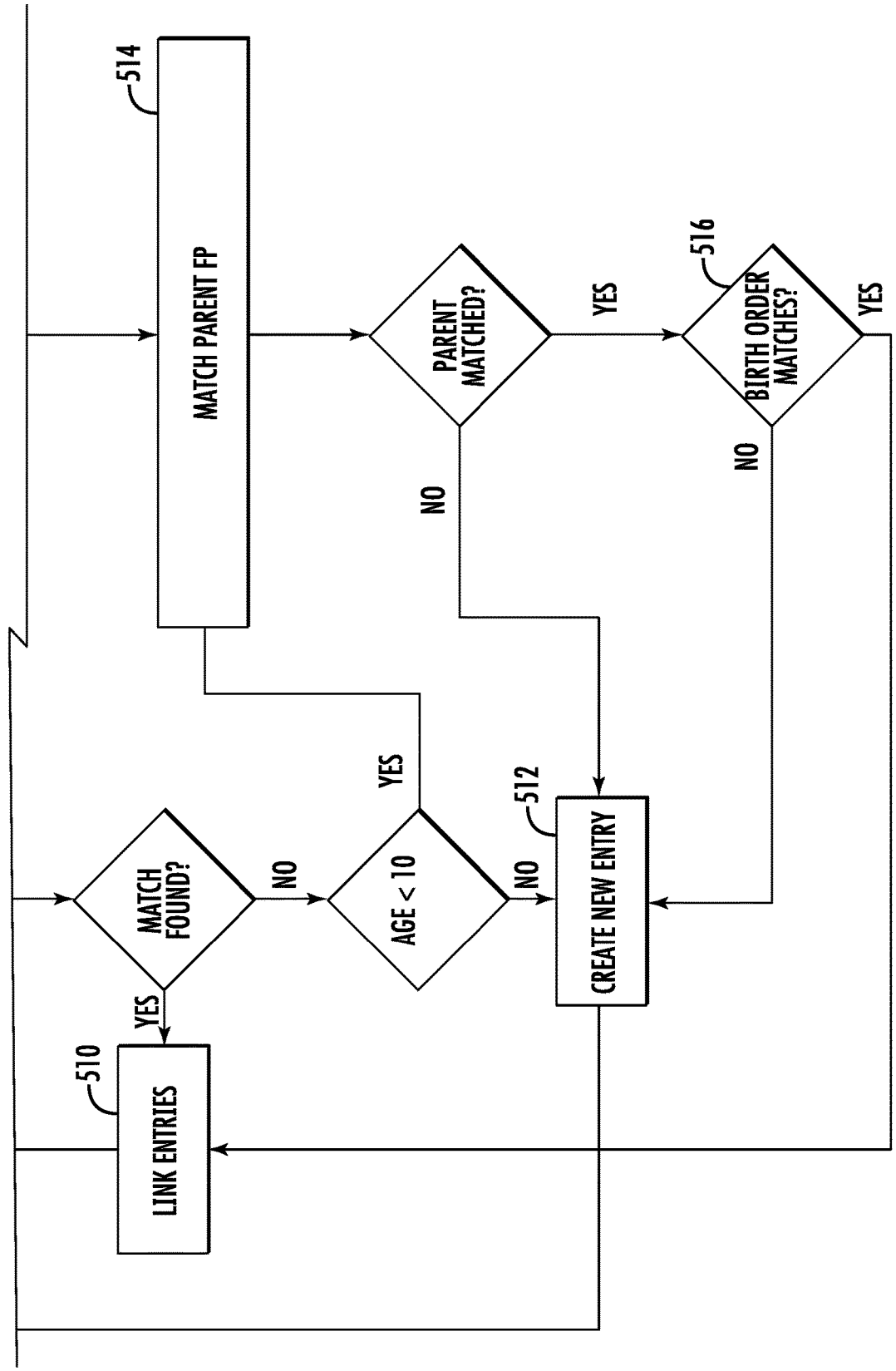
Figure 6:
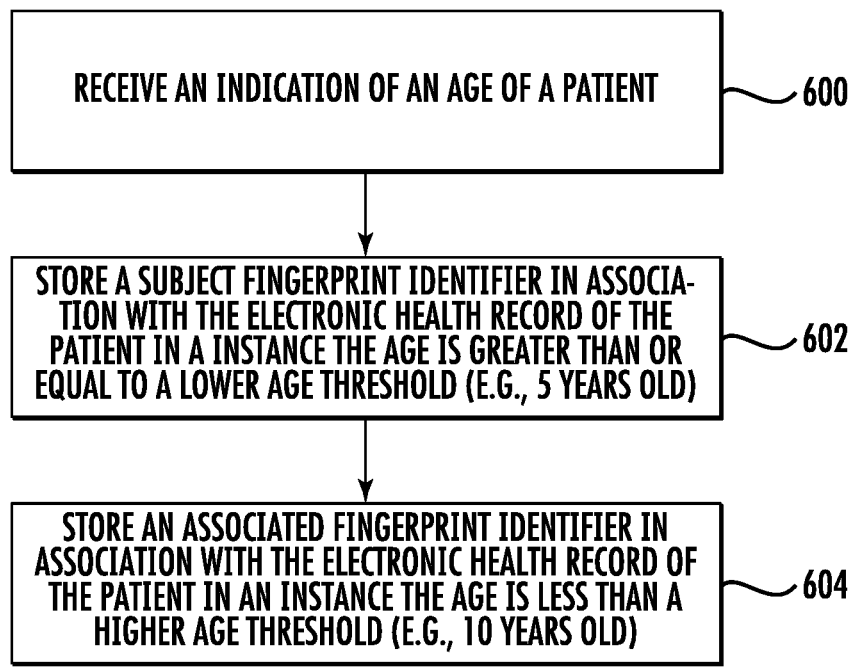
Figure 7A:
Figure 7B:
Figure 7C:
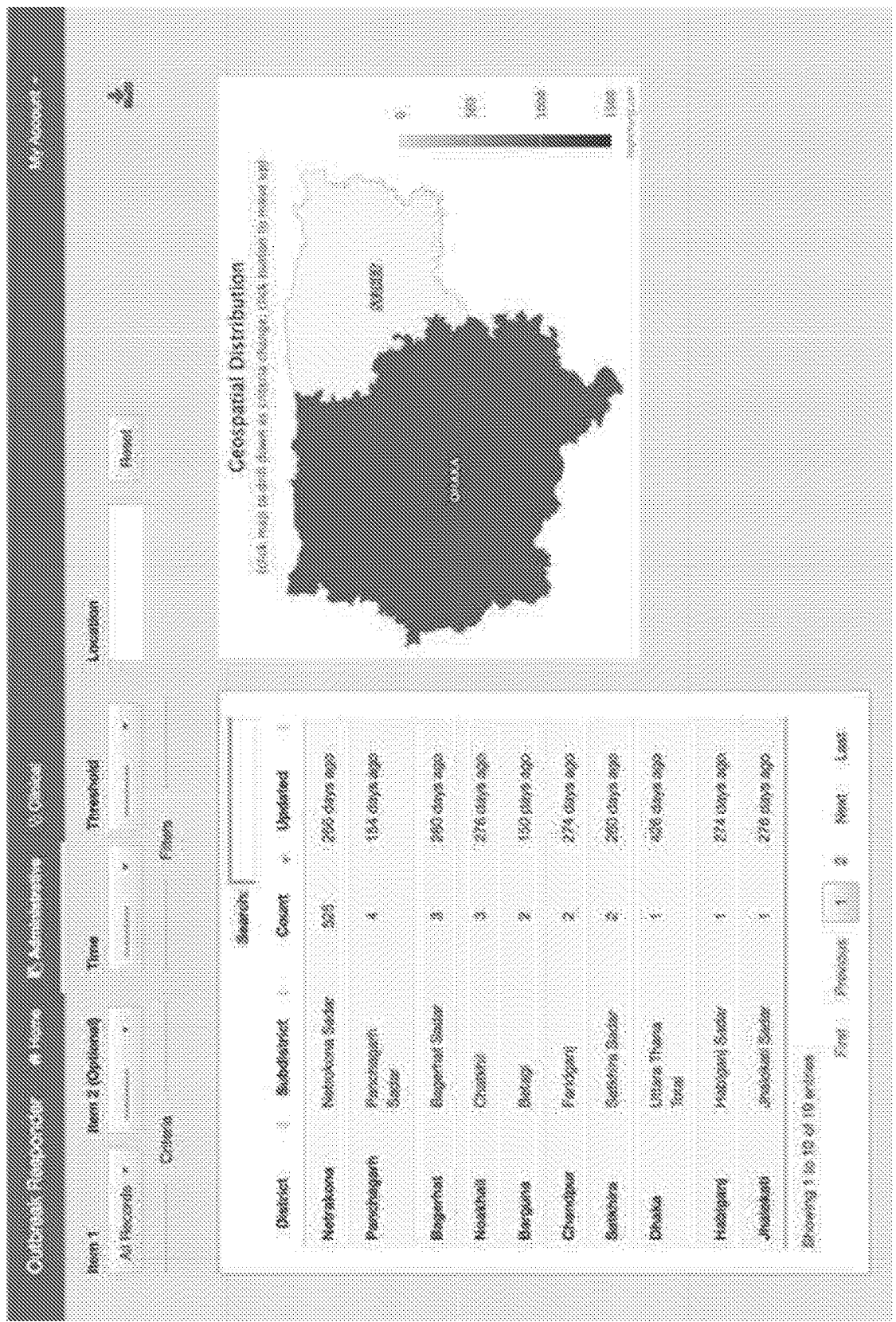

Having thus described certain example embodiments of the present invention in general terms, reference will hereinafter be made to the accompanying drawings which are not necessarily drawn to scale, and wherein:

FIG. 1 is an overview of a system that can be used to practice certain embodiments described herein;

FIG. 2 is an exemplary schematic diagram of an apparatus according to some example embodiments;

FIG. 3 provides a process by which a user is prompted to obtain electronic fingerprint data according to some example embodiments;

FIGS. 4A-4G illustrate example user interfaces in accordance with some example embodiments;

FIGS. 5A, 5B, and 6 provide flowcharts illustrating operations performed in accordance with some example embodiments;

FIGS. 7A-7C illustrate example user interfaces in accordance with some example embodiments; and FIGS. 8, 9A, 9B, and 10-12 provide flowcharts illustrating operations performed in accordance with some example embodiments.

DETAILED DESCRIPTION

Various embodiments now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout.

As described below, a method, apparatus and computer program product are provided for identifying individuals using electronic fingerprint data, providing residence mapping functionality, resolving conflicts relating to the update of electronic records, and optimizing performance relating to the access of electronic records. FIG. 1 is an overview of a system that can be used to practice certain embodiments described herein, and should not be considered limiting.

As illustrated in FIG. 1, example embodiments may be implemented as or employed in a distributed system. The various depicted components may be configured to communicate over a network 10, such as the Internet, for example, or any other communication interface as described in further detail hereinafter. In general, user device(s) 30 may be configured to communicate with a server 40 and/or database 50. User device 30 may include any computing device such as a smart phone, laptop, tablet, personal computer laptop and/or the like, and may be used by practitioners in the field to access a health information system provided via the server 40, which may access electronic health records, and other data on database 50.

The user device 30 may be configured to perform any of the operations described herein. In this regard, even during times of no network access or weak signal, users may access at least some or all functionality described herein with a user device 30. At periodic sync intervals, or as network access becomes available, data may be synchronized between the user device 30 and server 40 (which in turn may cause updates to and from the database 50).

The system of FIG. 1 described above is provided merely as an example implementation and it will be appreciated that the example embodiments provided herein may be implemented as or employed by any number of system architectures.

Referring now to FIG. 2, apparatus 200 is a computing device(s) configured for identifying individuals using electronic fingerprint data, providing residence mapping functionality, resolving conflicts relating to the update of electronic records, and optimizing performance relating to the access of electronic records according to example embodiments. Apparatus 200 may at least partially or wholly embody any of the network 10, user device 30, server 40, and/or database 50 described above.

Apparatus 200 may include or otherwise be in communication with a processor 210, user interface 212, communication interface 214, and memory 216. As describe above, apparatus 200 may be implemented as a distributed system for performing the operations described herein. As such, any of the components such as the processor 210, user interface 212, communication interface 214, and memory 216, or portion(s) thereof, may be distributed across multiple computing devices and may be collectively configured to operate as apparatus 200. As such, the various operations described herein may indeed be performed by different computing devices.

The processor 210 may, for example, be embodied as various means including one or more microprocessors with accompanying digital signal processor(s), one or more processor(s) without an accompanying digital signal processor, one or more coprocessors, one or more multi-core processors, one or more controllers, processing circuitry, one or more computers, various other processing elements including integrated circuits such as, for example, an ASIC (application specific integrated circuit) or FPGA (field programmable gate array), or some combination thereof. Accordingly, although illustrated in FIG. 2 as a single processor, in some embodiments processor 210 comprises a plurality of processors. The plurality of processors may be embodied on a single computing device, such as server 40, or may be distributed across a plurality of computing devices collectively configured to function as the processor 210. The plurality of processors may be in operative communication with each other and may be collectively configured to perform one or more functionalities as described herein. In an example embodiment, processor 210 is configured to execute instructions stored in memory 216 or otherwise accessible to processor 210. These instructions, when executed by processor 210, may cause the apparatus 200 to perform one or more of the functionalities as described herein.

Whether configured by hardware, firmware/software methods, or by a combination thereof, processor 210 may comprise an entity capable of performing operations according to the example embodiments described herein. Thus, for example, when processor 210 is embodied as an ASIC, FPGA or the like, processor 210 may comprise specifically configured hardware for conducting one or more operations described herein. Alternatively, as another example, when processor 210 is embodied as an executor of instructions, such as may be stored in memory 216, the instructions may specifically configure processor 210 to perform one or more algorithms and operations described herein.

Memory 216 may comprise, for example, volatile memory, non-volatile memory, or some combination thereof. Although illustrated in FIG. 2 as a single memory, memory 216 may comprise a plurality of memory components. The plurality of memory components may be embodied on a single computing device or distributed across a plurality of computing devices. Memory 216 may include database 50, for example, and/or any memory components of user device 30, and/or server 40. In various embodiments, memory 216 may comprise at least a non-transitory medium such as but limited to a hard disk, random access memory, cache memory, flash memory, a compact disc read only memory (CD-ROM), digital versatile disc read only memory (DVD-ROM), an optical disc, circuitry configured to store information, or some combination thereof. Memory 216 may be configured to store information, data (e.g., electronic health records), applications, instructions, or the like for enabling apparatus 200 to carry out various functions in accordance with example embodiments described herein. In some examples, data may be stored in memory 216 may be protected with the native encryption system on the device. For example, in at least some embodiments, memory 216 is configured to buffer input data for processing by processor 210. Additionally or alternatively, in at least some embodiments, memory 216 is configured to store program instructions for execution by processor 210. Memory 216 may store information in the form of static and/or dynamic information. This stored information may be stored and/or used by apparatus 200 during the course of performing its functionalities.

Communication interface 214 may be embodied as any device or means embodied in circuitry, hardware, a computer program product comprising computer readable program instructions stored on a computer readable medium (e.g., memory 216) and executed by a processing device (e.g., processor 210), or a combination thereof that is configured to receive and/or transmit data from/to another device and/or network, such as, for example, a second apparatus 200 and/or the like. In some embodiments, communication interface 214 (like other components discussed herein) can be at least partially embodied as or otherwise controlled by processor 210. In this regard, communication interface 214 may be in communication with processor 210, such as via a bus. Communication interface 214 may include, for example, an antenna, a transmitter, a receiver, a transceiver, network interface card and/or supporting hardware and/or firmware/software for enabling communications with another local or remote computing device and/or servers. Communication interface 214 may include a network (e.g., network 10), such as any wired or wireless communication network including a local area network (LAN), personal area network (PAN), wide area network (WAN), the Internet, an intranet, or the like, as well as any attendant hardware, software and/or firmware required to implement said networks (e.g. network routers and network switches). Communication interface 214 may be configured to receive and/or transmit any data that may be provided by computing devices such as the data distribution service 20, for example, using any protocol that may be used for communications between computing devices. Communication interface 214 may be further configured, for example, to write data to database 50. Communication interface 214 may additionally or alternatively be in communication with the memory 216, user interface 212 and/or any other component of apparatus 200, such as via a bus.

User interface 212 may be in communication with processor 210 to receive an indication of a user input and/or to provide an audible, visual, mechanical, or other output to a user. As such, user interface 212 may include, for example, a keyboard, a mouse, a user device, a computer, a display, and/or other input/output mechanisms. In embodiments in which apparatus 200 is embodied as a distributed system, user interface 212 may be implemented on a user device, such as user device 30, that may be separate from a server or other computing device configured to perform at least some of the operations described herein. For example, at least some aspects of user interface 212 may be embodied on an apparatus used by a user that is configured to communicate with apparatus 200. For example, the user interface 212 may be implemented at least partially on a user device, such as user device 30, and may be configured for accessing electronic health records in an online or offline mode, accessing other components of a health information system provided by server 40, and/or other operations as described herein. The user interface 212 may be in communication with memory 216, communication interface 214, and/or any other component(s), such as via a bus. One, or more than one, user interfaces 212 can be included in apparatus 200.

Identification Using Fingerprints

When a patient visits a clinic, a fingerprint scanning system may be used to identify the patient and match the patient to an existing electronic health record, or to associate the patient with a new electronic health record according to example embodiments. The fingerprint scanning system may include any fingerprint scanner, fingerprint recognition system, fingerprint authentication system, and/or fingerprint scanning system configured to capture a fingerprint of an individual, and to match the fingerprint to previously scanned fingerprints of the same individual. The fingerprint scanning system may be implemented to capture fingerprint data in a variety of ways, including but not limited to ink fingerprinting, electronic fingerprint scanning, or digital fingerprint scanning. The fingerprint scanning system may be integrated with a user device 30 operative in the clinical setting, and may be configured to communicate with server 40. In some examples, apparatus 200 may be configured to interface with the fingerprint scanning system such that the apparatus 200 recognizes a fingerprint as a unique numeric identifier. To do this, the fingerprint scanning system may generate this fingerprint identifier using an algorithm applied to the fingerprint data generated by scanning a corresponding fingerprint. The fingerprint identifier may thereafter be used by processor 210, stored on memory 216 (e.g., database 50) and/or the like as a representation of the fingerprint to avoid requiring use of an image of the fingerprint itself. The apparatus 200 may therefore utilize the fingerprint identifiers as described herein to associate a fingerprint with an electronic health record.

As introduced above, fingerprint scans of children may be difficult to obtain or, if obtained, may not be reliable or discernable by the system. FIG. 3 provides a process by which example embodiments prompt a user, such as a clinical assistant or practitioner, to follow in obtaining a patient's fingerprint(s) and/or fingerprint(s) of those associated with or accompanying the patient (e.g., a parent). The fingerprints will be used as described in further detail hereinafter, to link the fingerprint(s) to an electronic health record.

According to some example embodiments, and in an example scenario such as an instance in which a patient is a young child, the fingerprints of the other individuals may be used to identify the child. The age ranges and thresholds referred to in FIG. 3 and hereinafter used to determine whose fingerprints and of which hand are to be captured are provided merely as an example, and may be altered in some example embodiments. For example, age ranges described below include the ranges of ages 0-5, 5-10, and 10+. It will be appreciated, that other ranges may be used. For example, another possible set of age ranges used according to example embodiments include 0-11, 11-18, and 18+. In some examples, the set of age ranges, or any other age ranges, may be used to determine whether or not the individual may be presented with a digital consent.

Parents such as a mother and father are also referred to merely as examples of individuals who may likely be with the child in the clinic, but it will be appreciated that the fingerprints of any other individual accompanying the child may be used.

As illustrated in FIG. 3, age 10 may be considered a minimum or threshold age at which the patient's fingerprint alone (e.g., without an additional fingerprint of another individual) can be reliably used to identify the electronic health record. If the patient's age is greater or equal than 10 years old, example embodiments may prompt the user to request to obtain a fingerprint scan of the right fingerprint of the patient. If the user is uncertain as to the patient's age, the user may ask the patient's age.

Some example embodiments may be configured to capture and use a specific fingerprint of an individual, such as a fingerprint of the index finger. It will be appreciated, however, that any fingerprint may be used and any reference to a fingerprint of an index finger is not intended to be limiting.

If the patient's age is greater than or equal to 5 (which may be considered an example minimum or threshold age to begin obtaining patient fingerprints) but less than 10 years old, the user may obtain the patient's right fingerprint (e.g., right index fingerprint). In addition, the user may obtain a left fingerprint (e.g., left index fingerprint) of the mother, father or other individual accompanying the patient. The patient's right fingerprint along with the other individual's left fingerprint (e.g., left index fingerprint) may form a dyad of identifiers that will be associated with the patient's electronic health record, according to some example embodiments. In some embodiments and as described in further detail below, the patient's age, birth order, and/or gender may also be stored in associated with the fingerprint data and associated electronic health record.

If the patient's age is less than 5 years old, the user may not obtain the patient's fingerprint at all, but rather will be prompted to obtain the left fingerprint (e.g., the left index fingerprint) of the mother, father, and/or other individual accompanying the child. Age 5 is used merely as an example, and may be determined as a minimum age to obtain an individual's fingerprint, whether due to the difficulty in obtaining the fingerprint of child, and/or the fingerprint scanning system's difficulty in discerning a young child's fingerprint. The fingerprint identifier along with the patient's age, birth order, and/or gender as described in further detail below may be stored in association with the electronic health record.

FIGS. 4A-4G are example user interfaces that may be provided via user interface 212, such as may be implemented on user device 30. A user such as a medical practitioner or assistant may follow the guidance provided via the user interface to process a patient and to scan fingerprints. Referring to the user interface of FIG. 4A for guidance, a user may ask the patient associated questions to obtain the data, and enter a patient identifier or select 'none,' enter the patient's age, gender selection, and birth order (e.g., 1 for oldest child in family, and subsequent numerals based on birth order of the child). Residence information may also be obtained, using, for example, the methodology described below in connection with FIGS. 7A-7C and 8. In some embodiments, based on the entered patient age, and the decision tree of FIG. 3, the user may be prompted to register fingerprints. If fingerprint registration is selected, the user interface transitions to FIG. 4B. Based on a patient age of 6, the user is prompted to scan the right fingertip of the patient's index finger.

Figure 4A:
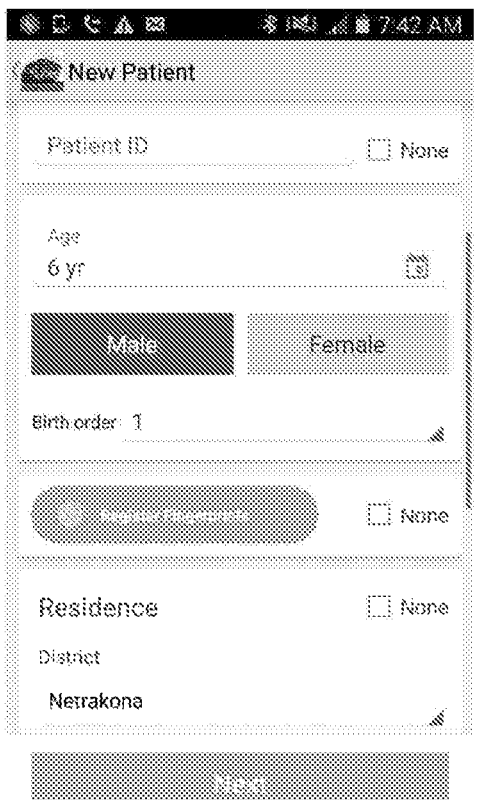
Figure 4B:
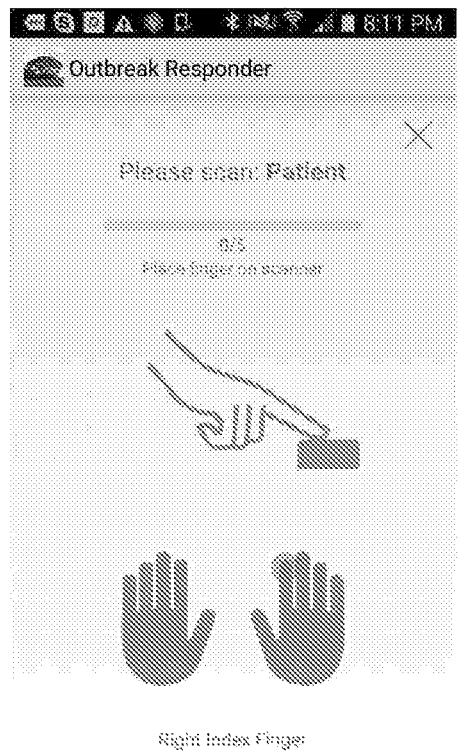
Figure 4C:
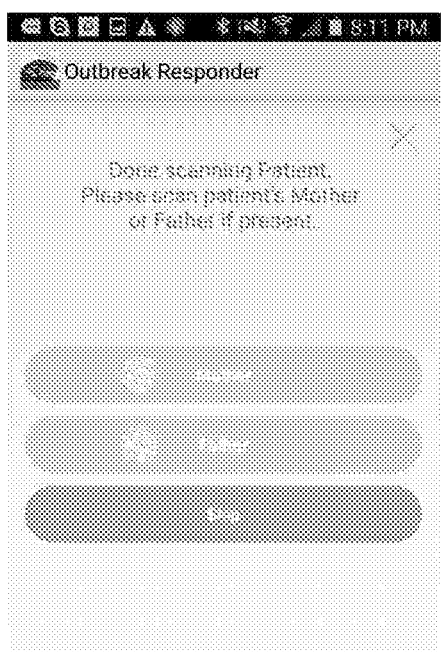
Figure 4D:
Figure 4E:
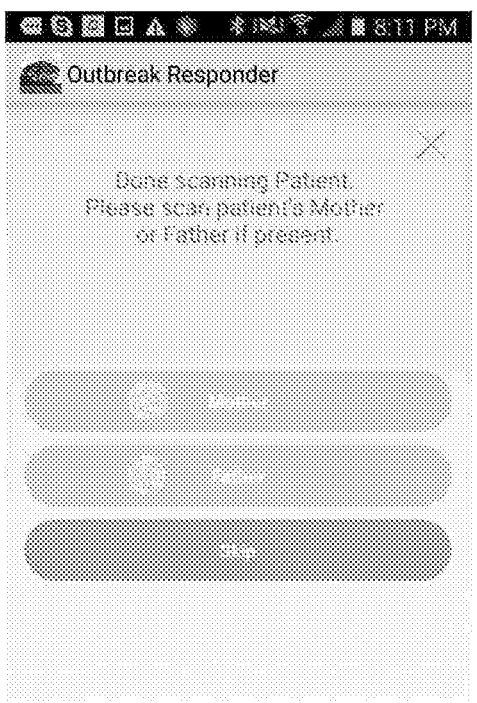
Figure 4F:
Figure 4G:
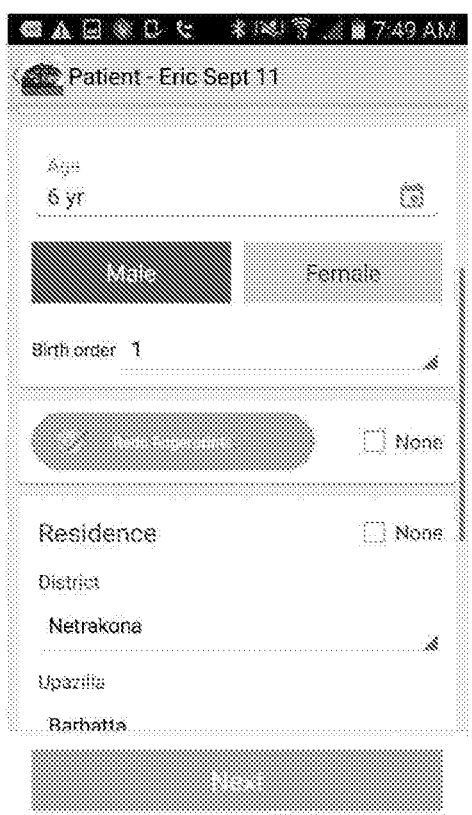

Using the user interface of FIG. 4C, the user may indicate whether the mother, father, or any other individual is present with the child and obtain a fingerprint of the other individual. Or, the user may skip this step (e.g., if parent fingerprints have been retrieved previously). If the user selects to scan another individual's fingerprint, the user interface transitions to that of FIG. 4D, by which the user is prompted to obtain a left index fingerprint scan of the other individual (e.g., mother). The user interfaces of FIGS. 4E and 4F may be similarly used to scan the father's left fingerprint. It will be understood that similar interfaces may be provided to facilitate scanning of the left fingerprint of another individual accompanying the child who is not the child's mother or father (e.g., a non-parent caretaker or relative). Completion of the fingerprint scanning process may result in a return to the patient information page provided in FIG. 4G.

The fingerprints captured with guidance of the user interfaces of FIGS. 4A-4G may be processed as set forth in FIGS. 5A and 5B to identify whether the patient information matches an existing electronic health record or if the system should create a new electronic health record to be associated with the patient. To determine if there is a match with an existing electronic health record, the apparatus 200 fetches (500) all existing records from database 50 with gender x as provided in the user interface. In some examples, all of the records from database 50 may be preloaded onto the user device 30 while the device is connected to a network, such that matching electronic health records can be retrieved in response to a subsequent request even when the user device is no longer connected to the network. Similarly, fingerprint data may be cached in association with newly captured electronic health record data for subsequent uploading and synchronization with server 40 and/or database 50. As described above, the fingerprint scanning software may capture a given fingerprint as an image or as other fingerprint data, and may transform the captured image or fingerprint data into a unique numeric fingerprint identifier for use by the apparatus 200, thus enabling the fingerprint identifier to thereafter be processed and transmitted by the apparatus 200 rather than requiring the additional resources that would otherwise be required to perform a fingerprint comparison. In any event, having fetched all records, and/or subset of records, of the appropriate gender from the database, the apparatus may determine whether there is new patient information for matching with the database records (502). Upon determining that the apparatus 200 was able to retrieve new patient information at 502, the apparatus 200 prepares the new patient information for a particular new patient for matching (504) by gathering one or more fingerprint identifier and associated demographic data entered via the user interface of the apparatus 200 for the particular new patient, as described in connection with FIGS. 4A-4G.

Upon determining that the patient age provided via the user interface is greater than 5, the apparatus 200, such as with processor 210, may attempt to match the patient fingerprint identifier to that of an existing record (506), and if a match is found, may link the new patient information associated with the corresponding electronic health record (510). The identified electronic health record may then be accessed as the electronic health record of the subject patient. If a match is not found, and the age is greater than or equal to 10, the apparatus 200 may create a new entry (e.g., electronic health record) including the new patient information for the particular new patient (512).

If no match is found at 506 but the patient age is less than 10, the apparatus 200 may further attempt to match a parent fingerprint (514). In this regard, apparatus 200 may also proceed to 514 instead of 506 to match the parent fingerprint (514) if the patient age is less than 5. If the parent fingerprint is not matched to a parent fingerprint of an existing electronic health record, apparatus 200 creates a new entry for the new patient that includes (512). If the parent fingerprint does match an existing parent fingerprint associated with an electronic health record, the apparatus 200 narrows the set of potentially matching records, and checks the birth order (516) of those remaining potentially matching records. If the birth order provided via the user interface matches the birth order of an electronic heath record in the remaining subset, then the matching electronic health record is linked to the patient (510), and may be retrieved for access, and/or associated with the patient and updated accordingly.

In the above example, the subject patient's fingerprint is obtained from the right hand, while the associated individuals' fingerprints are obtained from the left hand. This configuration is used as an example herein but it will be appreciated that fingerprints from either hand may be used.

FIG. 6 is a flowchart of operations performed by apparatus 200 according to some example embodiments. As shown by operation 600, apparatus 200, such as with processor 210, user interface 212, communication interface 214, memory 216 and/or the like, receives an indication of an age of a patient.

In operation 602, apparatus 200, such as with processor 210, communication interface 214, memory 216 and/or the like stores a subject fingerprint identifier in association with the electronic health record of the patient in an instance in which the age of the patient is greater than or equal to a lower age threshold (e.g., 5 years old).

In operation 604, apparatus 200, such as with processor 210, communication interface 214, memory 216 and/or the like stores an associated fingerprint identifier, such as a fingerprint identifier of a parent or other caretaker, in association with the electronic health record of the patient in an instance in which the age of the patient is less than a higher age threshold (e.g., 10 years old).

Operations 602 and 604 are not mutually exclusive, and one of the operations or both may be performed for a patient. The stored fingerprint identifiers may then be used in subsequent matching of fingerprints to electronic health records, as described above. The associations may further include information relating to any of age, gender, and birth order of the patient.

Example embodiments therefore improve the accuracy of patient to electronic health record matching, particularly in scenarios in which the patient is a young child and accurate fingerprints may be inconsistent or indiscernible.

Residence Mapping

FIGS. 7A and 7B are user interfaces that may be provided by apparatus 200 according to example embodiments. The user interfaces may be accessed to enter patient information including residence information. Some patients may not have addresses that are known to compatible mapping services and/or geographical information systems (GIS) or may not know how to convey their residential location using modes of communication standard in the U.S.

FIGS. 7A and 7B provide an alternative mode of residence mapping that relies upon a local model of residence identification in Bangladesh. A user may ask a patient for their district, upazilla (sub-district), union, and/or village. The information may be considered a culturally relevant location hierarchy, (e.g., also known as a gazetteer), and may be entered and stored in associated with the electronic health record of the patient. Additionally or alternatively, the apparatus 200 may store a treatment location, such as a location detected with a global position system (GPS) tracking unit of the user device 20, at the time of the patient encounter or, if the mobile device is unable to utilize a GPS tracking unit at the time of treatment, by using, as the treatment location, the location detected by the GPS tracking unit upon its next connection to a network, or alternatively, the most recent location detected by the GPS tracking unit prior to losing network connectivity.

Collecting the culturally relevant location hierarchy (e.g., district, upazilla, union and village) enables the system to store residence information describing where the patient lives. The residence information known to the patients may be un-mapped in commonly used geographical information systems. However, the culturally relevant location hierarchy (e.g., district, upazilla, union and village) may be subsequently mapped and made available to apparatus 200 to collect uniform residence information amongst patients. Additionally, even if the residence of the patient is mapped, the inventors have determined that providing the culturally relevant location hierarchy format to patients to enter their residence location can produce more accurate residence identification than would be conveyed by patients who are forced to identify their residence on a map provided by the apparatus 200, because many patients in remote areas like Bangladesh are not used to using maps but are nevertheless able to use the culturally relevant location hierarchy (e.g., district, upazilla, union and village) formulation. The apparatus 200 may therefore track and/or identify residence information related to otherwise un-mapped locations.

The culturally relevant location hierarchy may enable example embodiments to integrate with other GIS functionality and/or applications. For example, integration with GIS applications for use in remote or unmapped areas may result in problems or defects in the GIS applications due to the lack of accurate mappings available to the GIS application. For example, GIS applications allowing for selection or a "pin drop" on a displayed map may not accurately capture a physical address associated with the position of the selection or pin drop. However, when the GIS application is integrated according to example embodiments, an accurate location according to the culturally relevant location hierarchy may be identified and/or stored.

Further, with the captured residence information including the culturally relevant location hierarchy, example embodiments of apparatus 200, may provide and/or enable a user interface such as that of FIG. 7C. A user may enter criteria or select filters such as but not limited to time, threshold, and/or location. A listing of the numbers or counts of records matching the criteria and filters, may be provided, and may be sorted and/or grouped by any components of the culturally relevant location hierarchy, district, subdistrict, count, and the date or time elapsed since last updates to any of the associated records. A geospatial distribution may also be displayed, such as in the form of a heat map, showing the counts of electronic records meeting the specified criteria and/or filters, and distributed visually by geographic area and/or culturally relevant location hierarchy. A user may therefore utilize the user interface to view outbreaks or other medical trends in a geospatial arrangement. Further, a user may click the map to drill down to the selected geographic area, which may update the arrangement to display at a lower level (e.g., any component of the culturally relevant location hierarchy such as district, upazilla, union and village). A user may also select to view additional detail relating to the records associated with the selected area. In some embodiments, a displayed gazetteer may be auto-filled based on the data selected and/or entered at higher levels of the gazetteer (e.g., higher levels of the culturally relevant location hierarchy).

Figure 8:
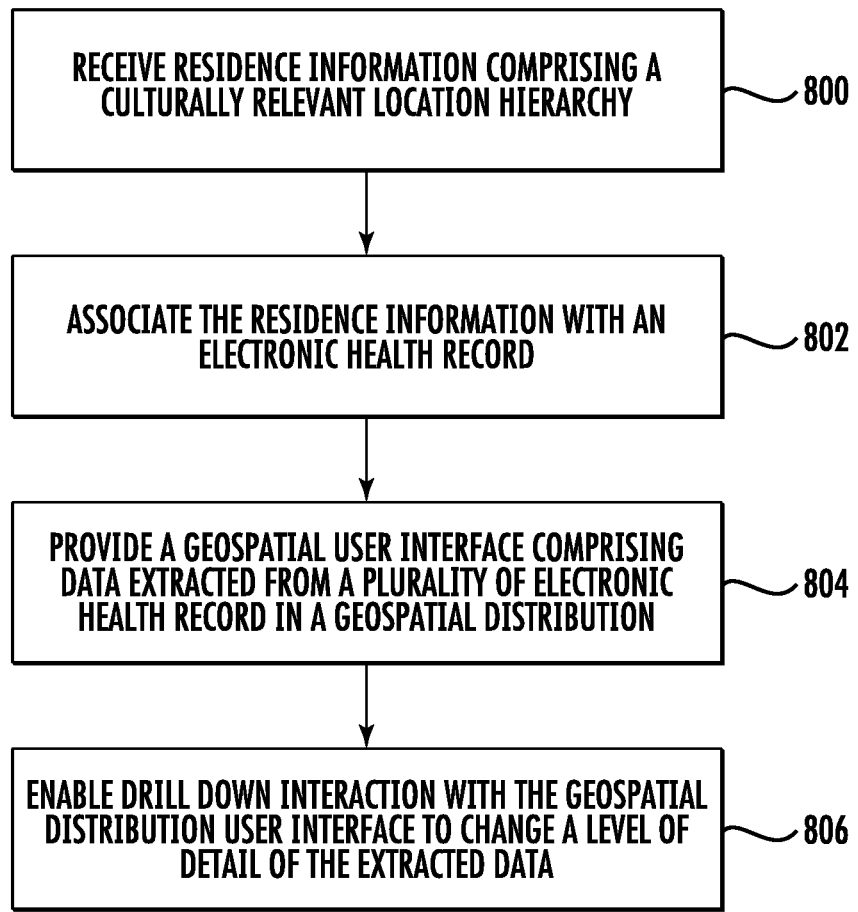

FIG. 8 is a flowchart of operations performed by apparatus 200 according to some example embodiments. At operation 800, apparatus 200, such as with processor 210, user interface 212, communication interface 214, memory 216 and/or the like, receives residence information comprising a culturally relevant location hierarchy (e.g., district, upazilla, union and/or village). At operation 802, apparatus 200, such as with processor 210, communication interface 214, memory 216 and/or the like, associates the residence information with an electronic health record. At operation 804, apparatus 200, such as with processor 210, user interface 212, communication interface 214, memory 216 and/or the like, provides a geospatial distribution user interface comprising data extracted from a plurality of electronic health records in a geospatial distribution user interface. At operation 806, apparatus 200, such as with processor 210, user interface 212, communication interface 214, memory 216 and/or the like, enables drill down interaction with the geospatial distribution user interface to change a level of detail of the extracted data.

Example embodiments therefore provide for more accurate geospatial representation of medical data, even when many patients reside in remote villages that may not coincide with the mappings otherwise known to the clinical system or underlying geographic information system.

Conflict Resolution

Figure 9A:
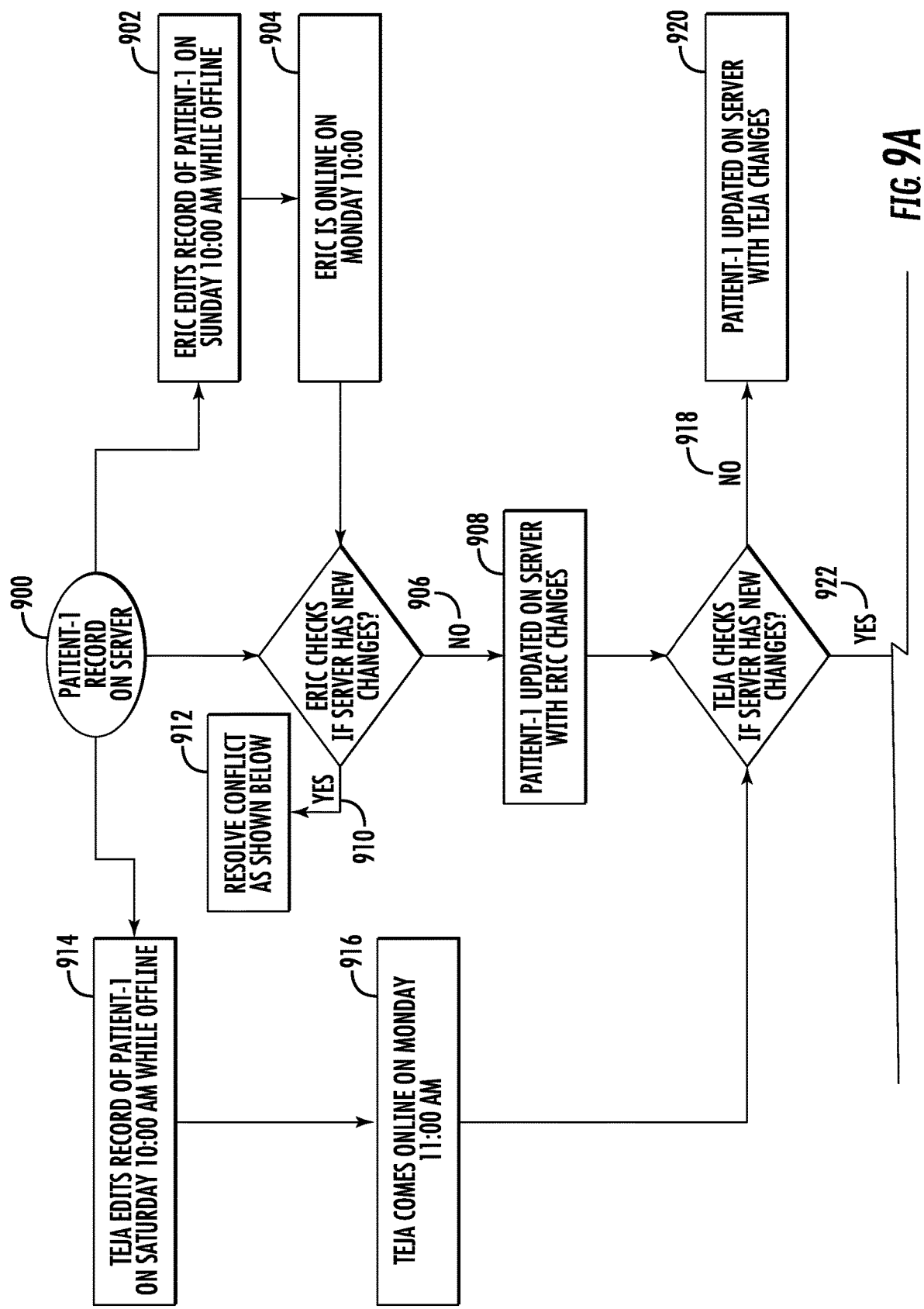
Figure 9B:
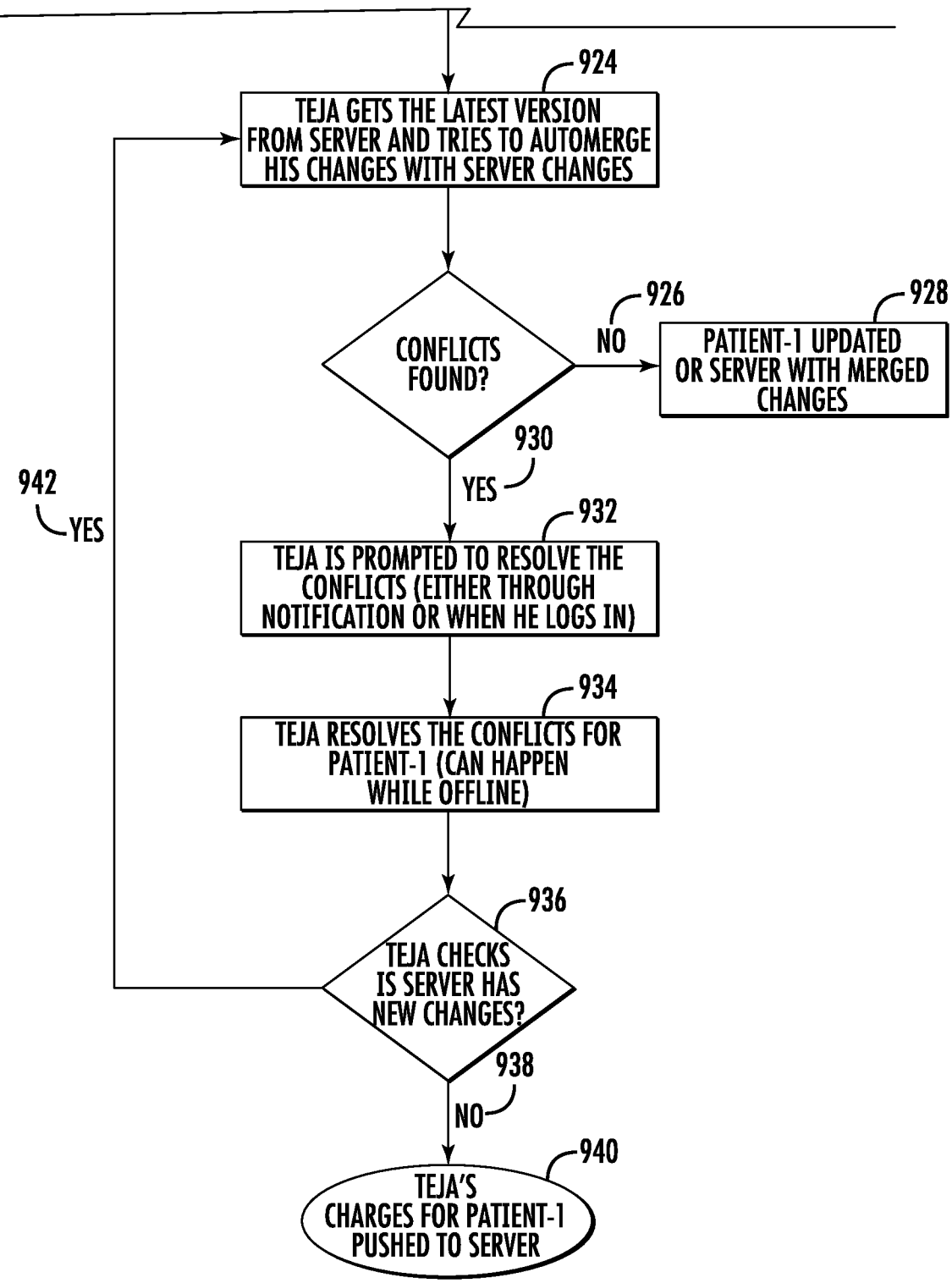

As introduced above, multiple users may update electronic health records in an offline mode, creating data conflicts when returning to an online mode. FIGS. 9A and 9B provide a flowchart of example user interactions resulting in a conflict, and operations performed by apparatus 200 for resolving such conflicts, according to some example embodiments. An electronic health record, "patient-1 record," may be downloaded from server 40 (900) to various user devices 30. At a later time, a first user, Eric, edits the patient-1 record on Sunday at 10 am while offline (902). On Monday at 10 am, Eric's user device returns to a state of being online or having network access (904). The user device 30 accesses the server 40, and apparatus 200 determines changes to patient-1 record have not been made since the patient-1 record was downloaded (906). The patient-1 record is therefore updated on the server with Eric's changes (908). If it is determined that another change has been made to patient-1 record (910), operation 912 proceeds to operation 924, described below.

In the example shown in FIGS. 9A and 9B, Teja has edited the same patient-1 record on Saturday 10 am while also offline (914) and then comes online on Monday at 11 am (916). If Eric's changes had not been made to the same patient-1 record and patient-1 record had not been updated since Teja's retrieval of the patient-1 record (918), Teja's changes would be made to patient-1 record on the server (920).

However, considering the provided example days and times of Eric's and Teja's updates and return to online access, Teja comes online after Eric, and Eric's changes to patient-1 record have already been made on the server (922). In this case, the latest version from the server (which would include Eric's changes) are downloaded from the server 40 to the user device 30, and example embodiments auto-merge the changes (924). For instance, if Eric and Teja edited different fields of the patient-1 record, the auto-merger will determine that no actual conflict exists and can incorporate the changes made by Teja automatically. Alternatively, if Eric or Teja is predefined (e.g., by title, duties, hardcoding into the system, or the like) as having greater authority regarding edits to any particular fields that both have edited, the edits regarding the conflicting field that are from the user having greater authority may be automatically retained while the edits to the conflicting field from the other user are discarded. If no conflicts in the patient-1 record and/or particular fields of the patient-1 record are found (926) or the auto-merger resolves any identified conflicts, the auto-merged changes are merged to the patient-1 record on the server 40 (928). If conflicts in the patient-1 record and/or particular fields of the patient-1 record are found (930), example embodiments prompt Teja to resolve the conflict, such as through notification, or when he logs into the system (932). Teja utilizes the user interface, provided according to example embodiments, to resolve the conflict and confirm the correct data will be included in the patient-1 record (934). Example embodiments then check if any additional changes have been made to patient-1 record on the server (936). If not (938), the resolved changes to patient-1 record on user device 30 are uploaded or pushed to the server 40

(940). If additional changes have been made to patient-1 record on the server (942), the process returns to 924.

Figure 10:
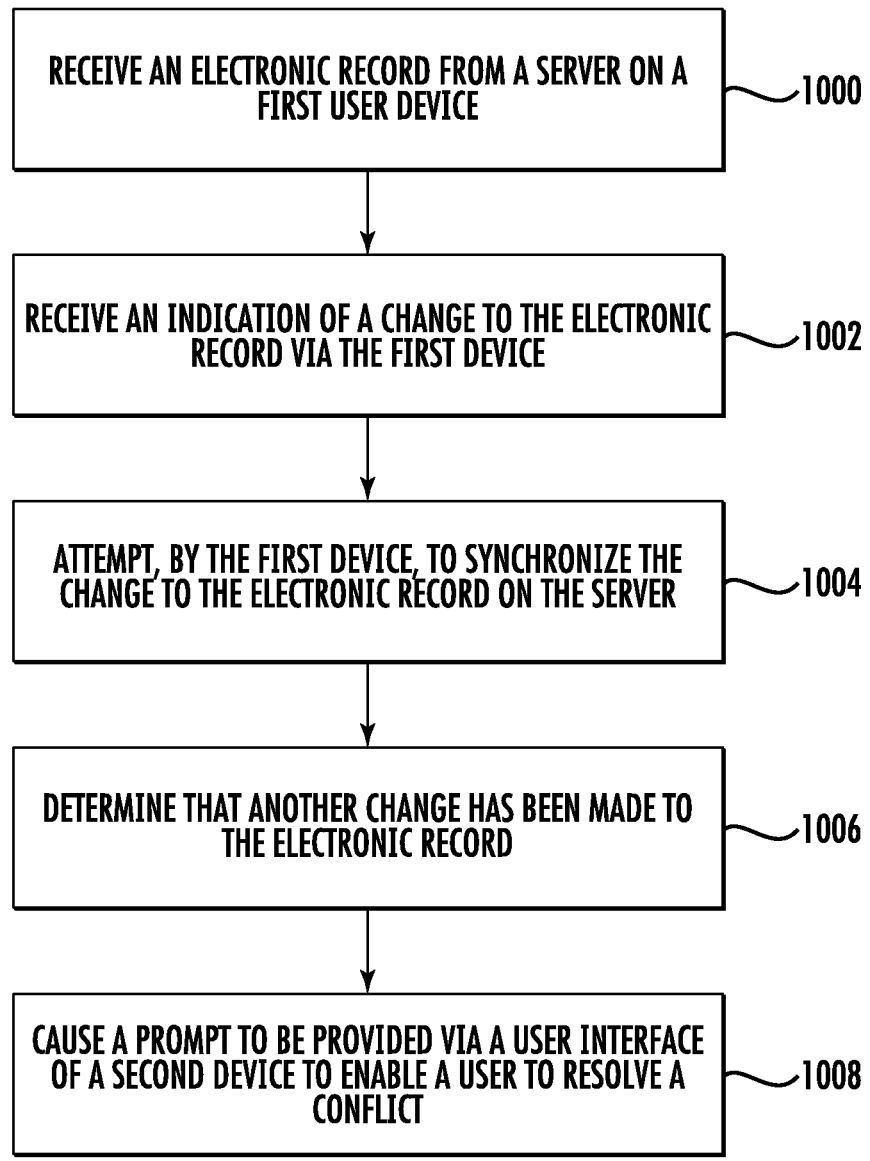

FIG. 10 is a flowchart of operations performed by apparatus 200 according to some example embodiments. At operation 1000, apparatus 200, such as with processor 210, user interface 212, communication interface 214, memory 216 and/or the like receives an electronic record (e.g., electronic health record) from a server, such as server 40, on a first user device 30. The record may be stored or cached on the user device and the first user device 30 may access the electronic record even when the device is not connected to the network.

At operation 1002, apparatus 200, such as with processor 210, user interface 212, communication interface 214, memory 216 and/or the like, receives an indication of a change to the electronic record via the first device. At operation 1004, apparatus 200, such as with processor 210, user interface 212, communication interface 214, memory 216 and/or the like attempts, by the first device, to synchronize the change to the electronic record on the server. At operation 1006, apparatus 200, such as with processor 210, user interface 212, communication interface 214, memory 216 and/or the like, determines determine that another change has been made to the electronic record. If an auto-merge operation resolves the conflict, then the procedure concludes at operation 1004. Otherwise, the procedure advances to operation 1008. At operation 1008, apparatus 200, such as with processor 210, user interface 212, communication interface 214, memory 216 and/or the like, causes a prompt to be provided via a user interface of a second device to enable a user to resolve a conflict. The user may provide input to resolve the conflict. Changes are made to the electronic record as directed by the user. As another example, example embodiments may determine the accurate data point during conflict based on the user's working role or relationship (administrator, doctor, receptionist, nurse, etc.)

Example embodiments therefore improve data integrity in the electronic health records by detecting conflicts and enabling a user to correct or confirm conflicting data.

Optimization During Weak or No Signal

Figure 11:
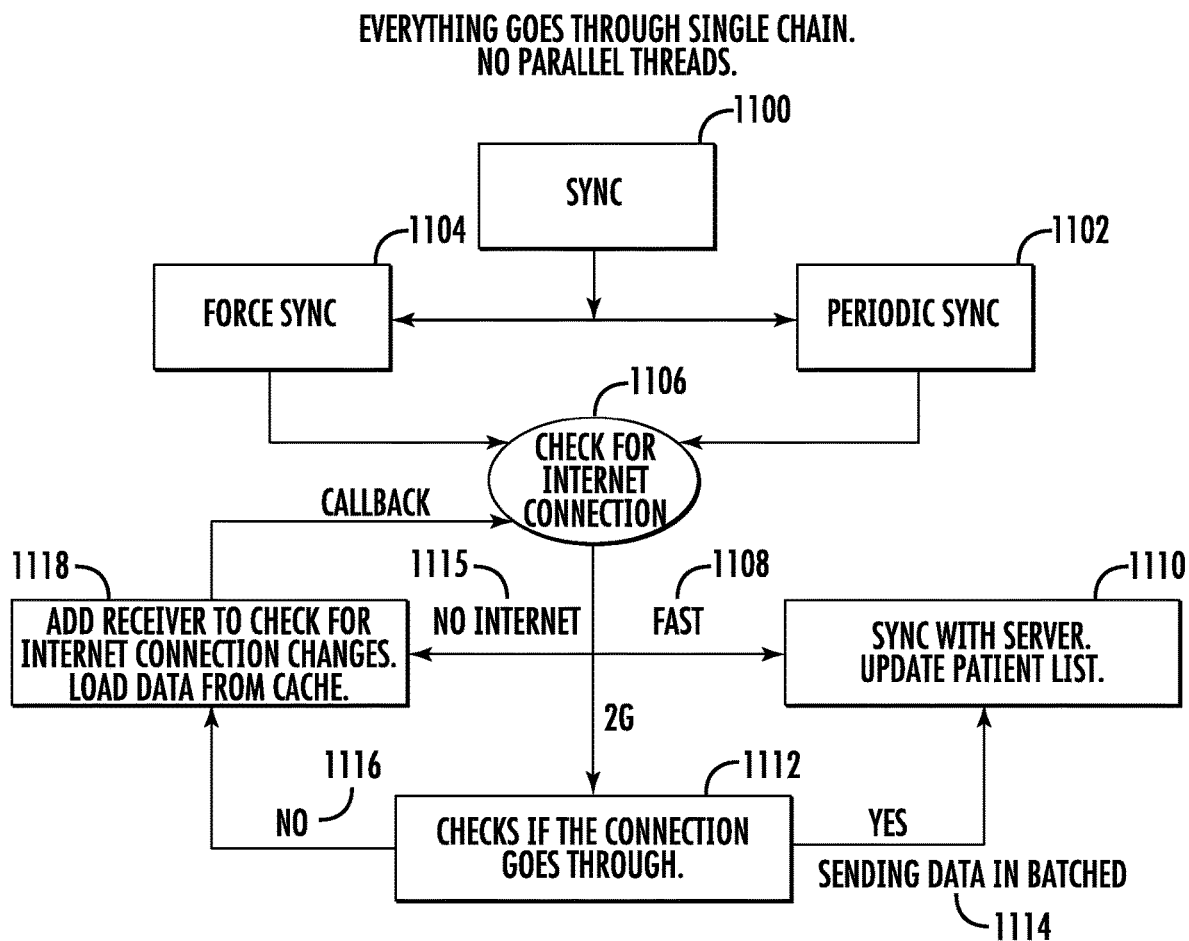

FIG. 11 is a flowchart of operations that may be performed according to some example embodiments for optimizing synchronization between user devices 30 and server 40 when there is a weak or no network connection. The data may be transmitted via a single chain such that no parallel threads are utilized. A sync 1100 may be performed periodically (1102) or may be forced (1104) by user input, for example. Apparatus 200 may check for an Internet connection (1106). If the connection is fast or strong (1108), such as may be determined based on detection of a strong local area network signal (e.g., Wi-Fi), the apparatus may synchronize its local patient data (e.g., locally stored patient information and/or electronic health record) with the server 40 and/or database 50 in a single synchronization procedure (1110). If the signal is weak, such as 2G or a weak local area network signal, apparatus 200 attempts to connect to server 40 (1112). If the apparatus 200 can connect, data is sent in batches (1114) to be synced with the server as a sequence of multiple distinct synchronization procedures (1110). When there is no network connection (1115) or the 2G or other weak connection is not sufficient to sync with the server (1116), apparatus 200 adds a receiver to check for internet connection changes (1118). The data to be synced may be cached. The apparatus 200 may monitor the connection for improvements and attempt to connect via 1106. The receiver may check for improved connected at a frequent time interval (e.g., every 5 minutes) until a connection and sync is performed, whereas a periodic sync (1102) may only occur at a less frequent time interval (e.g., every hour).

Figure 12:
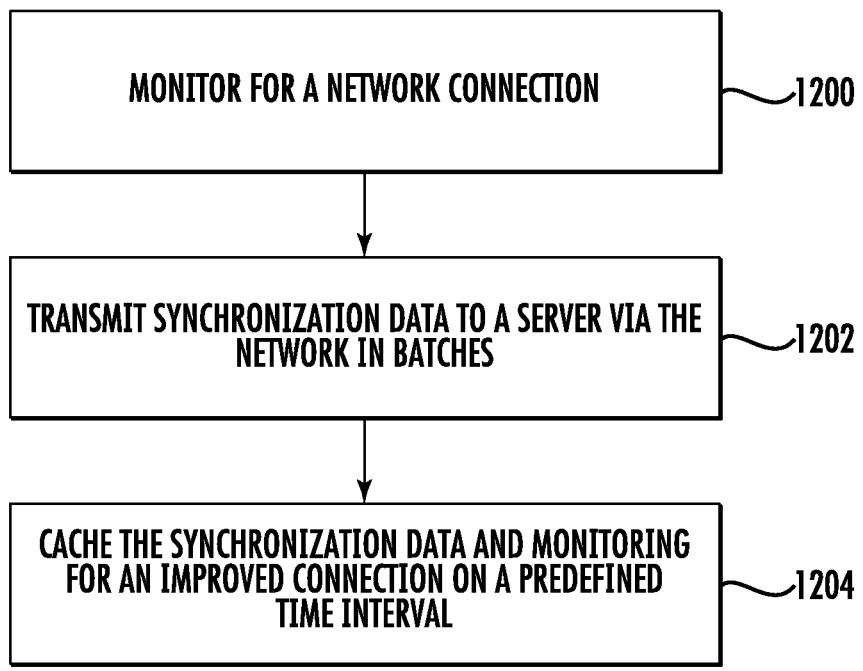

FIG. 12 is a flowchart of operations performed by apparatus 200 according to some example embodiments. At operation 1200, apparatus 200, such as with processor 210, communication interface 214, memory 216 and/or the like, monitors for a network connection. As noted in connection with FIG. 11, this may be done via a forced synchronization request or in response to a periodic synchronization request. In an instance in which a fast network connection is identified, data is synced with server 40 in a single synchronization procedure. However, in an instance in which the network connection speed is identified and is below a predefined threshold and above or equal to a minimum threshold, the procedure advances to operation 1202. Finally, in an instance in which the network connection speed is below the minimum threshold or no connection is available, the procedure advances to operation 1204. At operation 1202, apparatus 200, such as with processor 210, communication interface 214, memory 216 and/or the like, determines to transmit data via the network in batches, such that the data is synced with server 40 in a series of multiple distinct synchronization procedures. At operation 1204, apparatus 200, such as with processor 210, communication interface 214, memory 216 and/or the like, caches the data and checks for an improved connection on a predefined time interval until the data is transmitted. In some embodiments, this predefined time interval is more frequent than the periodic interval of a periodic synchronization setting.

According to the example, during times of strong connectivity, the periodic sync may only occur every hour. The attempted synchronization every 5 minutes will only occur when a period sync is missed, and may be stopped once the sync is performed. The dynamic behavior for synchronization enables example embodiments to optimize performance and preserve battery life, while providing adequate data synchronization between the server and user devices.

CONCLUSION

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method performed by at least a processor, for linking a patient to an electronic health record and requesting to retrieve the electronic health record by utilizing fingerprints of one or both of the patient or an individual accompanying the patient dependent on an age of the patient, and determining which of a left or right fingerprint to utilize dependent on whether the respective fingerprint is of the patient or the individual accompanying the patient, the method comprising:

defining primary fingerprint identifiers as taken from one of left or right hands, and opposite fingerprint identifiers as taken from the opposite of the left or right hand as the primary fingerprint identifiers;

linking the patient to the electronic health record by:
(a) in response to the processor determining that a first presented age of the patient is greater than, or greater than or equal to a lower age threshold, storing, in a database, a primary fingerprint identifier of the patient, in association with the electronic health record of the patient; and
(b) in response to the processor determining that the first presented age is less than, or less than or equal to a higher age threshold storing, in the database, an opposite fingerprint identifier of the individual accompanying the patient in association with the electronic health record of the patient; and requesting to retrieve the electronic health record from the database by querying the database with a request generated by:
(a) receiving an indication of a second presented age of the patient;
(b) in response to the processor determining that the second presented age of the patient is less than, or less than or equal to the higher age threshold, including in the request an opposite fingerprint identifier of the second presented individual accompanying the patient; and
(c) in response to the processor determining that the second presented age of the patient is greater than, or greater than or equal to the lower age threshold, including in the request the primary fingerprint identifier of the patient.

2. The method of claim 1, wherein the primary subject fingerprint identifier and the opposite fingerprint identifier comprise unique numeric identifiers.

3. The method according to claim 1, wherein the method further comprises: in response to the processor determining that (a) the first presented age of the patient is greater than, or greater than or equal to a lower age threshold, and (b) the first presented age is less than, or less than or equal to a higher age threshold, storing, in the database, both the primary fingerprint identifier of the patient and the opposite fingerprint identifier of the individual accompanying the patient in association with the electronic health record of the patient.

4. The method according to claim 1, wherein in response to the processor determining that (a) the second presented age of the patient is less than, or less than or equal to the higher age threshold and (b) the second presented age of the patient is greater than, or greater than or equal to the lower age threshold, the request to retrieve the electronic health record comprises both the opposite fingerprint identifier of the second presented individual accompanying the patient, and the primary fingerprint identifier of the patient.

5. The method of claim 1, further comprising:
in an instance no matching electronic health record is retrieved in response to the query, storing a new electronic health record in association with the one or more of the opposite fingerprint identifier of the second presented individual accompanying the patient, or the primary fingerprint identifier of the patient.

6. An apparatus for linking a patient to an electronic health record and requesting to retrieve the electronic health record by utilizing fingerprints of one or both of the patient or an individual accompanying the patient dependent on an age of the patient, and determining which of a left or right fingerprint to utilize dependent on whether the respective fingerprint is of the patient or the individual accompanying the patient, the apparatus comprising at least one processor and at least one memory including computer program code, the at least one memory and the computer program code configured to, with the processor, cause the apparatus to at least:

define primary fingerprint identifiers as taken from one of left or right hands, and opposite fingerprint identifiers as taken from the opposite of the left or right hand as the primary fingerprint identifiers;

link the patient to the electronic health record by:
(a) in response to the processor determining that a first presented age of the patient is greater than, or greater than or equal to a lower age threshold, storing, in a database, a primary fingerprint identifier of the patient, in association with the electronic health record of the patient; and
(b) in response to the processor determining that the first presented age is less than, or less than or equal to a higher age threshold storing, in the database, an opposite fingerprint identifier of the individual accompanying the patient in association with the electronic health record of the patient; and request to retrieve the electronic health record from the database by querying the database with a request generated by:
(a) receiving an indication of a second presented age of the patient;
(b) in response to the processor determining that the second presented age of the patient is less than, or less than or equal to the higher age threshold, including in the request an opposite fingerprint identifier of the second presented individual accompanying the patient; and
(c) in response to the processor determining that the second presented age of the patient is greater than, or greater than or equal to the lower age threshold, including in the request the primary fingerprint identifier of the patient.

7. The apparatus of claim 6, wherein the primary subject fingerprint identifier and the opposite fingerprint identifier comprise unique numeric identifiers.

8. The apparatus of claim 6, wherein in response to the processor determining that (a) the first presented age of the patient is greater than, or greater than or equal to a lower age threshold, and (b) the first presented age is less than, or less than or equal to a higher age threshold, the at least one memory and the computer program code are further configured to, with the processor, cause the apparatus to at least store in the database both the primary fingerprint identifier of the patient and the opposite fingerprint identifier of the individual accompanying the patient in association with the electronic health record of the patient.

9. The apparatus of claim 6, wherein in response to the processor determining that (a) the second presented age of the patient is less than, or less than or equal to the higher age threshold and (b) the second presented age of the patient is greater than, or greater than or equal to the lower age threshold, the request to retrieve the electronic health record comprises both the opposite fingerprint identifier of the second presented individual accompanying the patient, and the primary fingerprint identifier of the patient.

10. The apparatus of claim 6, wherein the at least one memory and the computer program code are further configured to, with the processor, cause the apparatus to at least:
in response to determining no matching electronic health record is retrieved in response to the query, store a new electronic health record in association with the one or more of the opposite fingerprint identifier of the second presented individual accompanying the patient, or the primary fingerprint identifier of the patient.

11. An computer program product for linking a patient to an electronic health record and requesting to retrieve the electronic health record by utilizing fingerprints of one or both of the patient or an individual accompanying the patient dependent on an age of the patient, and determining which of a left or right fingerprint to utilize dependent on whether the respective fingerprint is of the patient or the individual accompanying the patient, the computer program product comprising at least one non-transitory computer-readable storage medium having computer-executable program code instructions stored therein, the computer-executable program code instructions comprising program code instructions to:

define primary fingerprint identifiers as taken from one of left or right hands, and opposite fingerprint identifiers as taken from the opposite of the left or right hand as the primary fingerprint identifiers;

link the patient to the electronic health record by:
 (a) in response to determining that a first presented age of the patient is greater than, or greater than or equal to a lower age threshold, storing, in a database, a primary fingerprint identifier of the patient, in association with the electronic health record of the patient; and
 (b) in response to determining that the first presented age is less than, or less than or equal to a higher age threshold storing, in the database, an opposite fingerprint identifier of the individual accompanying the patient in association with the electronic health record of the patient; and request to retrieve the electronic health record from the database by querying the database with a request generated by:
 (a) receiving an indication of a second presented age of the patient;
 (b) in response to determining that the second presented age of the patient is less than, or less than or equal to the higher age threshold, including in the request an opposite fingerprint identifier of the second presented individual accompanying the patient; and
 (c) in response to determining that the second presented age of the patient is greater than, or greater than or equal to the lower age threshold, including in the request the primary fingerprint identifier of the patient.

12. The computer program product of claim 11, wherein the first subject fingerprint identifier and the first associated fingerprint identifier comprise unique numeric identifiers.

13. The computer program product of claim 11, wherein in response to determining that (a) the first presented age of the patient is greater than, or greater than or equal to a lower age threshold, and (b) the first presented age is less than, or less than or equal to a higher age threshold, the computer-executable program code instructions further comprise program code instructions to store in the database both the primary fingerprint identifier of the patient and the opposite fingerprint identifier of the individual accompanying the patient in association with the electronic health record of the patient.

14. The computer program product of claim 11, wherein in response to determining that (a) the second presented age of the patient is less than, or less than or equal to the higher age threshold and (b) the second presented age of the patient is greater than, or greater than or equal to the lower age threshold, the request to retrieve the electronic health record comprises both the opposite fingerprint identifier of the second presented individual accompanying the patient, and the primary fingerprint identifier of the patient.

15. The computer program product of claim 11, wherein the computer-executable program code instructions further comprise program code instructions to:

in response to determining no matching electronic health record is retrieved in response to the query, store a new electronic health record in association with the one or more of the opposite fingerprint identifier of the second presented individual accompanying the patient, or the primary fingerprint identifier of the patient.

\* \* \* \* \*